(12) United States Patent
Howell et al.

(10) Patent No.: US 7,148,385 B2
(45) Date of Patent: Dec. 12, 2006

(54) PERFLUOROPOLYETHER PRIMARY BROMIDES AND LODIDES

(75) Inventors: Jon L. Howell, Bear, DE (US); Erik W. Perez, Middletown, DE (US); Alfred Waterfeld, Tuscaloosa, AL (US); Chadron Mark Friesen, Langley (CA); Joseph Stuart Thrasher, Tuscaloosa, AL (US); Ireneusz Nowak, Provo, UT (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 521 days.

(21) Appl. No.: 10/626,972

(22) Filed: Jul. 25, 2003

(65) Prior Publication Data

US 2004/0024250 A1 Feb. 5, 2004

Related U.S. Application Data

(60) Division of application No. 10/237,345, filed on Sep. 9, 2002, now Pat. No. 6,653,511, which is a continuation-in-part of application No. 09/901,927, filed on Jul. 10, 2001, now abandoned.

(51) Int. Cl.
*C07C 43/11* (2006.01)
(52) U.S. Cl. ............... 568/615; 568/604; 568/614; 568/591; 525/326.4
(58) Field of Classification Search ............... 568/615, 568/604, 614, 591; 525/326.4
See application file for complete search history.

(56) References Cited

U.S. PATENT DOCUMENTS

| | | |
|---|---|---|
| 3,505,411 A | 4/1970 | Rice |
| 3,682,876 A | 8/1972 | Anderson et al. |
| 4,973,762 A | 11/1990 | Tohzuka et al. |
| 5,278,340 A | 1/1994 | Koike et al. |
| 5,288,376 A | 2/1994 | Oyama et al. |
| 5,302,760 A | 4/1994 | Gschwender et al. |
| 5,453,549 A | 9/1995 | Koike et al. |
| 5,777,174 A | 7/1998 | Marchionni et al. |

OTHER PUBLICATIONS

R.N. Haszeldine, New General Methods for the Synthesis of Fluoroiodides and Fluoroacids, Nature, vol. 166, 192-193, 1950.
R.N. Haszeldine, The Reaction of Metallic Salts of Acids with Halogens. Part I. The Reaction of Metal Trifluoroacetates with Iodine, Bromine, and Chlorine, Metal Salts of Acids with Halogens. Part I, pp. 584-586, 1951.
Paskovich et al, Simplified Method for the Preparation of Fluoroalkyl lodides, J. Fluorine Chem. vol. 32, 833-834, 1967.
Zhao Cgengxue et al, Thermal Decomposition of Some Perfluoro- and Polyfluorodiacyl Peroxides, J. Org. Chem. vol. 47, 2009-2013, 1982.
A. Probat et al, Synthesis and Chemistry of Perfluoro-2-iodo-2-Methyl-Alkanes, J. Fluorine Chem. vol. 37, 223-245, 1987.
A. Probat et al, Thermolysis and UV-Photolysis of Perfluorinated Iodo-Alkanes and iodo-Oxaalkanes: There is a Preferred Reaction Channel, J. Fluorine Chem. vol. 47, 163-173, 1990.
H.K. Nair et al, Solvent effects on the reaction of Perfluoroalkyl iodides and α,ω-perfluoroalkyl diiodides with cadmium poeder and dimethylcadmium, J. Fluorine Chem. vol. 60, 1-12, 1993.
G.J. Chen et al, Perfluoroallkyulations and perfluorooxaalylations. Part 2., Copper-mediated cross-coupling of secondary perfluooxaalkyl iodides and aryl halides, J. fluorine Chem. vol. 65, 59-65, 1993.
H. Fukaya et al, Synthesis of new nitrogen-containing perfluoroalkyl iodides, J. Fluorine Chem., vol. 83, 117-123, 1997.

*Primary Examiner*—Elvis O. Price

(57) ABSTRACT

A perfluoropolyether and a composition comprising the perfluoropolyether are provided in which the perfluoropolyether comprises at least one bromine or iodine atom at the primary position of the perfluoropolyether. Also provided is a process for producing the composition in which the process comprises contacting a perfluoropolyether acid fluoride moiety with a metal bromide or metal iodide or a suitable polyether secondary iodide under a condition sufficient to effect the production of a perfluoropolyether comprising at least one bromine or iodine at the primary position.

11 Claims, No Drawings

PERFLUOROPOLYETHER PRIMARY BROMIDES AND LODIDES

This is a divisional application of Ser. No. 10/237,345, filed Sep. 9, 2002, now U.S. Pat. No. 6,653,511 allowed, which is a continuation-in-part application of Ser. No. 09/901,927, filed Jul. 10, 2001, abandoned.

FIELD OF THE INVENTION

The invention replaces to a perfluoropolyether primary bromide or iodide and to a process therefor.

BACKGROUND OF THE INVENTION

The trademarks and trade names used herein are shown in upper cases.

Perfluoropolyether primary bromides and iodides are a family of highly useful and reactive chemicals that can be used, for example, as lubricants, surfactants, and additives for lubricants and surfactants. See, e.g., *Journal of Fluorine Chemistry* 1999, 93, 1 and 2001, 108, 147 (hereinafter "Brace"). Brace discloses addition of iodides to alkenes, alkynes, allyls, etc to produce secondary iodides that have limited uses. Brace does not disclose the synthesis of valuable primary perfluoropolyether iodides.

The Hundsdiecker reaction (*Journal of Organic Chemistry* 1967, 32, 833) deals with reacting silver salts of the perfluoroalkyl carboxylic acid with free iodine. Such a reaction involves expensive reagents and is of limited commercial utility. *Journal of Fluorine Chemistry* 1993, 65, 59 (hereinafter "Eapen") discloses converting a hexafluoropropylene oxide (HFPO) tetramer acid fluoride to a secondary iodide. See also, U.S. Pat. Nos. 5,278,340 and 5,288,376 (halogen exchange of the fluorine in the acid fluoride with iodine using metal iodides and aprotic/polar solvent and exposing the acid iodide to ultraviolet irradiation, forming only the secondary iodide).

*Journal of Fluorine Chemistry* 1997, 83, 117 discloses exposing a molar excess of lithium iodide to low molecular weight perfluoroether acid fluorides at 180° C. for at least 6.5 hours to produce two low molecular weight perfluoropolyether iodides, one primary and one secondary.

U.S. Pat. No. 5,453,549 discloses a low molecular weight ethylene derivative of a primary iodide. It does not disclose the value of higher molecular weight products. Nor does it disclose the method of synthesis of the starting materials.

*Journal of Fluorine Chemistry*, 1990, 47, 163 discloses the feasibility of the formation of a primary iodide, in the gas phase, from dimer and trimer of hexafluoropropylene oxide.

While a polyfluorocarbon acid halide can likewise be converted to an iodide in a perhalogenated solvent using iodine and a metal carbonate, U.S. Pat. No. 4,973,762, subsequent removal of the solvent can be expensive and undesired traces can be left behind.

Mono-functional (Φ-CF(CF$_3$)CF$_2$OCF(CF$_3$)C(O)—F; Formula I) and di-functional (FC(O)CF(CF$_3$)OCF$_2$CF(CF$_3$)-Φ'-CF(CF$_3$)CF$_2$OCF(CF$_3$)C(O)F; Formula II) acid fluorides, which can be used in the present invention can be prepared according to Moore, U.S. Pat. No. 3,332,826 and Koike et al., U.S. Pat. No. 5,278,340 where Φ and Φ' are respectively monovalent and divalent perfluoropolyether moieties. Additionally, other acid fluorides of Formulae I and II are the reaction products formed from the polymerization of hexafluoropropylene oxide alone or with suitable starting materials, 2,2,3,3-tetrafluorooxetane, or the photo-oxidation of hexafluoropropylene or tetrafluoroethylene.

Secondary iodides from said acid fluorides can be prepared, for example at 0–60° C. using radiation from a photochemical lamp (for instance a lamp with an ultra-violet light output in the wavelength range of 220–280 nm (U.S. Pat. No. 5,288,376)).

The usefulness of this invention is demonstrated, for example, by the reactions of primary perfluoropolyether iodides with bromobenzene which could lead directly to perfluoropolyether substituted bromobenzene without the use of toxic or pyrophoric chemicals such as sulfur tetrafluoride or butyl lithium. These functionalized perfluoropolyether (PFPE) intermediates are used to form readily soluble, high temperature additives for fluorinated oils in boundary lubrication, as disclosed in Eapen and U.S. Pat. No. 5,550,277. These primary bromides or iodides described herein can also be used as intermediates in the production of fluorous phase media for applications such as catalysis (Horváth, I., Acc. Chem. Res. 1998, 31, 641) or separations (Curran, D. P. Angew. Chem., Int. Ed. Engl. 1998, 37, 1174), fluorosurfactants, and mold release agents.

Because there are few useful perfluoropolyether primary bromides or iodides and processes for producing them are not readily available to one skilled in the art, there is an ever increasing need to develop such products and processes.

SUMMARY OF THE INVENTION

A perfluoropolyether and a composition comprising the perfluoropolyether are provided in which the perfluoropolyether comprises at least one halogen atom at the primary position of one or more end groups of the perfluoropolyether and the halogen atom is bromine or iodine.

Also provided is a process for producing the composition in which the process comprises contacting either (1) a perfluoropolyether acid fluoride with a metal bromide or metal iodide or (2) heating a perfluoropolyether secondary halide under a condition sufficient to effect the production of a perfluoropolyether comprising at least one bromine or iodine at the primary position of one or more end groups of the perfluoropolyether.

DETAILED DESCRIPTION OF THE INVENTION

A common characteristic of perfluoropolyethers is the presence of perfluoroalkyl ether moieties. Perfluoropolyether is synonymous to perfluoropolyalkylether. Other synonymous terms frequently used include "PFPE", "PFPE oil", "PFPE fluid", and "PFPAE".

Examples of the inventive perfluoropolyether primary bromide or iodide include, but are not limited to, those having the formulae of

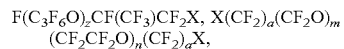

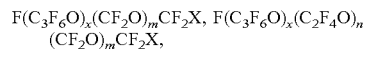

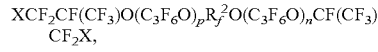

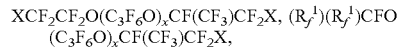

and combinations of two or more thereof where X is I or Br; x is a number from 2 to about 100; z is a number of about 5 to about 100, preferably 5 to about 100, more preferably at least about 6, and even more preferably 6 to 90, or 8 to 90 such as, for example, about 6, about 7, about 8, or about 52; p is a number from 2 to about 50, n is a number from 2 to about 50, m is a number from 2 to about 50, a is 1 or 2, each $R_f^1$ can be the same or different and is independently a monovalent $C_1$ to $C_{20}$ branched or linear fluoroalkanes, $R_f^2$ is a divalent $C_1$ to $C_{20}$ branched or linear fluoroalkanes, and $C_3F_6O$ is linear or branched.

The composition of the invention can be produced by any means known to one skilled in the art. It is preferred that it be produced by the process disclosed herein.

According to the invention, a process for producing the composition disclosed above can comprise, consist essentially of, or consist of contacting either (1) a perfluoropolyether acid fluoride or diacid fluoride containing a COF moiety with a metal bromide or metal iodide or (2) heating a perfluoropolyether secondary halide under a condition sufficient to effect the production of a perfluoropolyether comprising at least one bromine or iodine at the primary position of one or more end groups of the perfluoropolyether. The process generally involves a β-scission reaction. The process is preferably carried out under a condition or in a medium that is substantially free of a solvent or iodine or both. The process can also be carried out substantially free of a metal salt that is not a metal halide.

The acid fluoride including monoacid fluoride and diacid fluoride of Formula I and II, respectively, can be contacted with a metal iodide such as lithium iodide, calcium iodide, or barium iodide to make either a secondary or primary perfluoropolyalkylether iodide with the evolution of carbon monoxide and formation of the metal fluoride according to Reaction 1 for the monofunctional acid fluoride and Reaction 2 for the difunctional acid fluoride. These reactions can be carried out at or above about 180° C., preferably at or above about 220° C.

Φ-CF(CF₃)CF₂OCF(CF₃)C(O)—F+M$_{(1/v)}$I→Φ-CF(CF₃)CF₂—I+M$_{(1/v)}$F+CO+CF₃C(O)F     Reaction 1

FC(O)CF(CF₃)OCF₂CF(CF₃)-Φ'-CF(CF₃)CF₂OCF(CF₃)C(O)F+2M$_{(1/v)}$I→ICF₂CF(CF₃)-Φ'-CF(CF₃)CF₂I+2M$_{(1/v)}$F+2CO+2CF₃C(O)F     Reaction 2 where Φ, Φ' are as previously described, M is a metal selected from Li, Ca, or Ba, and v is the valency of the metal M.

A perfluoropolyether acid fluoride containing a —CF₂OCF(CF₃)COF moiety can be combined with a metal bromide or metal iodide under a condition sufficient to effect the production of a perfluoropolyether primary bromide or iodide. The metal moiety can be an alkali metal, an alkaline earth metal, or combinations of two or more thereof. Examples of suitable metal bromide and metal iodide include but are not limited to, lithium iodide, calcium iodide, barium iodide, aluminum iodide, boron iodide, aluminum bromide, boron bromide, and combinations of two or more thereof. The conditions can include an elevated temperature such as, for example, at or above about 180° C., preferably at or above about 220° C., under a pressure that can accommodate the temperature for a sufficient time period such as, for example, about 1 hour to about 30 hours.

The process can also comprise contacting a perfluoropolyether acid fluoride containing a COF moiety in the secondary position such as, for example, CF(CF₃)CF₂OCF(CF₃)COF, with a bromide or iodide MX under the conditions disclosed above.

According to the invention, the perfluoropolyether that can be used in the process of the invention can also comprise repeat units derived from the group consisting of —CF₂O—,
—CF₂CF₂O—, —CF₂CF(CF₃)O—, —CF(CF₃)O—, —CF(CF₃)CF₂O—, —CF₂CF₂CF₂O—, —CF(CF$_s$)O—, —CF₂CF(CF$_s$)O—, —CF₂CF(CF₂CF₃)O—, —CF₂CF(CF₂CF₂CF₃)O—, —CF(CF₂CF₃)O—, —CF(CF₂CF₂CF₃)O—, —CH₂CF₂CF₂O—, —CF(Cl)CF₂CF₂O—, —CF(H)CF₂CF₂O—, CCl₂CF₂CF₂O—, —CH(Cl)CF₂CF₂O—, and combinations of two or more thereof.

Perfluoropolyether containing these repeat units are well known to one skilled in the art. For example, KRYTOX available from E. I. du Pont de Nemours and Company comprises the repeat units of —CF(CF₃)CF₂O—.

The following examples illustrate the invention process.

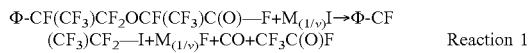
CF₂I (monofunctional), or

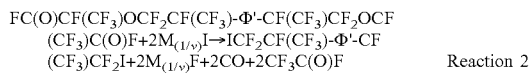
$_n$CF(CF₃)CF₂I (difunctional).

PFPE primary iodides can also be converted to their respective PFPE primary bromides by contacting them with carbon tetrabromide, for example, at 180° C. according to
F(C₃F₆O)$_z$CF(CF₃)CF₂I+CBr₄→F(C₃F₆O)$_z$CF(CF₃)CF₂Br+½I₂+½C₂Br₆.

PFPE acid fluorides can also be converted to their respective acid bromides by contacting them with mixed metal bromides such as, for example, aluminum bromide mixed with boron bromide. The acid bromide can be isolated. The isolated acid bromide can be heated at elevated temperature such as, for example, about 340° C.

The following examples illustrate this invention.

EXAMPLES

Example 1

Preparation of CF₃(CF₂)₂(OCF(CF₃)CF₂)$_{(n-1)}$OCF(CF₃)CF₂I from the corresponding secondary iodide CF₃(CF₂)₂(OCF(CF₃)CF₂)$_n$OCF(CF₃)I having n~8.

The polyhexafluoropropylene oxide homopolymer (HFPO) secondary iodide, CF₃(CF₂)₂(OCF(CF₃)CF₂)$_n$OCF(CF₃)I having n~8, used as the starting material in this example, was made by first adding lithium iodide (Aldrich Chemical, Milwaukee, Wis. (117.78 g) to a nitrogen-purged 2-L PYREX round-bottomed flask. KRYTOX Acid Fluoride (907.18 g) (available from E. I. du Pont de Nemours and Company, Wilmington, Del.) was then added to the flask, and the mixture was heated at 180° C. for 15 hours with stirring. The oil was filtered through a CELITE bed and analyzed by mass spectrometry and ¹³C NMR spectroscopy. From the mass spectrum, fragments at 227 m/z (—CFICF₃) and 393 m/z (—CF(CF₃)CF₂OCFICF₃) are indicative of the secondary iodide. Nuclear magnetic resonance (NMR) analysis showed the carbon bonded to iodine at 78.1 ppm d,q; —CFICF₃; ¹J$_{CFI}$=314.8 Hz, ²J$_{CF3}$=43.3 Hz (¹³C NMR: 75.5 MHz, D₂O/TMS).

Polyhexafluoropropylene oxide homopolymer (HFPO) secondary iodide (200.0 g, prepared as above) was added to a 500-mL PYREX round-bottomed flask and heated to 220° C. for 4 hours with stirring. The oil was filtered through CELITE (a SiO₂ filter aid), and analyzed by mass spectrometry and ¹³C NMR spectroscopy. The HFPO primary iodide was identified by mass spectrometry analysis, mass fragments of m/z=277 (—CF(CF₃)CF₂I) and m/z=177 (—CF₂I) prove the structure of the desired product. By ¹³C NMR spectroscopy, peaks specific to the desired product were detected at 93.8 ppm (t,d, —CF(CF₃)CF₂I, ¹J$_{CF}$=332.94 Hz, ²J$_{CF}$=33.19 Hz) and at 93.9 ppm (t,d, —CF(CF₃)CF₂I, ¹J$_{CF}$=332.94 Hz, ²J$_{CF}$=33.19 Hz). Yield: 187.0 g.

Example 2

Preparation of $CF_3(CF_2)_2(OCF(CF_3)CF_2)_{(n-1)}OCF(CF_3)CF_2I$ from KRYTOX Acid Fluoride having n~8.

Lithium iodide (187.71 g) was added to a nitrogen purged 2-L PYREX round-bottomed flask. Upon addition of KRYTOX Acid Fluoride (1,651.3 g), the flask was heated at 220° C. for 15 hours with stirring. The oil was filtered through CELITE and determined to be identical to the above product. Yield 1447.6 g.

Example 3

Preparation of $CF_3(CF_2)_2(OCF(CF_3)CF_2)_{(n-1)}OCF(CF_3)CF_2I$ from KRYTOX Acid Fluoride having n~8.

Calcium iodide (Aldrich Chemical, Milwaukee, Wis.) (20.72 g) was added to a nitrogen purged 500-mL round-bottomed flask in a dry box. Next, KRYTOX Acid Fluoride (100.00 g) was added, and the mixture was heated at 220° C. for 12 hours with stirring. The product was allowed to cool to room temperature and was filtered through CELITE. The product was consistent with earlier results. Yield 60.62 g.

Example 4

Preparation of $CF_3(CF_2)_2(OCF(CF_3)CF_2)_{(n-1)}OCF(CF_3)CF_2I$ from KRYTOX Acid Fluoride having n~6.

Barium iodide (Aldrich Chemical, Milwaukee, Wis.) (5.00 g) was added to a nitrogen purged 50-mL round-bottomed flask. Next, KRYTOX Acid Fluoride (13.1 g) was added to the flask. The reaction mixture was heated at 220° C. for 12 hours while stirring. The primary iodide was identified by GC/MS and was consistent with earlier results. Yield: 5.1 g.

Example 5

Preparation of $CF_3(CF_2)_2(OCF(CF_3)CF_2)_{(n-1)}OCF(CF_3)CF_2I$ from KRYTOX Acid Fluoride having n~52.

Lithium iodide (52.0 g) was added to a nitrogen purged 5-L PYREX round-bottomed flask. Upon addition of KRYTOX Acid Fluoride (2720 g), the mixture was heated at 220° C. for 20 hours with stirring. The oil was filtered through CELITE and determined to be the desired products. Yield 2231.76 g.

Example 6

Preparation of $CF_3(CF_2)_2(OCF(CF_3)CF_2)_{(n-1)}OCF(CF_3)CF_2Br$ from the corresponding acid fluoride.

Step 1. 5.57 g $F(CF(CF_3)CF_2O)_5CF(CF_3)COF$, 0.53 g $AlBr_3$ (Aldrich Chemical, Milwaukee, Wis.), and 2.65 g $BBr_3$ (Aldrich Chemical, Milwaukee, Wis.) were loaded into a 75-ml stainless steel cylinder in a glove box. The cylinder was closed with a valve and kept at ambient temperature for 24 h with occasional shaking. After that, the liquid content was removed with a pipette and filtered. The subsequent $^{13}C$ NMR spectroscopy shows quantitative conversion of the Acid Fluoride to the acid bromide.

Step 2. Conversion of the acid bromide to the HFPO primary bromide. 3.82 g of product from above was loaded into a 75-ml stainless steel cylinder within a glove box, closed with a valve, evacuated, weighed, and heated to 250° C. for 16 h. Additional heating to 340° C. overnight produced 0.08 g CO and other volatiles. Investigation of the liquid residue by $^{13}C$ NMR spectroscopy showed total disappearance of the acid bromide and new signals for the primary bromide. Along with the other signals expected, the chemical shift for the —$CF_2Br$ carbon is found at δ=115.6 ppm; t, d; $^1J_{CF2}$=313.8 Hz, $^2J_{CF}$=32.5 Hz thus establishing the identity of the desired product.

Example 7

Preparation of $CF_3(CF_2)_2(OCF(CF_3)CF_2)_nOCF(CF_3)CF_2Br$ from the corresponding Iodide.

Poly(hexafluoropropylene oxide) primary iodide (469.3 g) prepared, as in Example 3, was added to a nitrogen purged 500-ml round-bottomed flask. With stirring, carbon tetrabromide (Aldrich Chemical, Milwaukee, Wis.) (115.9 g) was charged to the flask and heated slowly to 175–185° C. and held at that temperature for 3 days. The primary bromide was identified by mass spectrometry, with mass fragments of m/z=229 and m/z=231 (—$CF(CF_3)CF_2Br$) and m/z=129 and m/z=131 (—$CF_2Br$) being indicative of the HFPO primary bromide. Yield: 299 g.

Comparative Example A (Method A) A thermal reaction was attempted between KRYTOX Acid Fluoride and sodium iodide (Aldrich Chemical, Milwaukee, Wis.) at a temperature of 220° C. Sodium iodide (27.11 g) and KRYTOX Acid Fluoride (186.34 g) were added to a nitrogen purged 500-ml round-bottomed flask equipped a thermocouple and reflux condenser. The reactants were heated at 220° C. for 12 hours while stirring. The product was filtered through CELITE and analyzed with mass spectrometry. No reaction was observed.

(Method B) A reaction was attempted between KRYTOX Acid Fluoride, sodium iodide, and acetonitrile at 50° C. to reproduce prior art as reported in U.S. Pat. No. 5,278,340. Sodium iodide (42.85 g) and KRYTOX Acid Fluoride (160.00 g) were added to a nitrogen purged 250-ml round-bottomed flask equipped with a thermocouple and reflux condenser. Next, acetonitrile (7.00 g) was added. The reactants were stirred while heating at 50° C. for 12 hours. The product was filtered through CELITE and analyzed by mass spectrometry. No reaction was observed.

Comparative Example A demonstrates that sodium iodide alone or sodium iodide dissolved in acetonitrile does not form a poly(hexafluoropropylene oxide) iodide.

Comparative Example B

Potassium iodide (Aldrich Chemical, Milwaukee, Wis.) (36.52 g) was added to a nitrogen purged 500-ml round-bottomed flask and heated at 110° C. for 30 min to dry the salt. Next, KRYTOX Acid Fluoride (226.79 g) was added to the flask and the contents of the flask were heated at 180° C. for 12 hours. After the reaction, the product was filtered through CELITE and analyzed by mass spectrometry. No reaction was observed.

Comparative Example B demonstrates that potassium iodide cannot be used to form a poly(hexafluoropropylene oxide) iodide.

Comparative Example C

Lithium bromide (Aldrich Chemical, Milwaukee, Wis.) (25.0 g) was added to a nitrogen purged 50-ml round-bottomed flask. Next, KRYTOX Acid Fluoride (149.0 g) was added to the reaction flask. The reaction mixture was heated at 220° C. for 12 hours with stirring. The product was washed with methanol, then water, and analyzed by mass spectrometry. No reaction was observed.

Comparative Example C demonstrates that lithium bromide cannot be used to form a poly(hexafluoropropylene oxide) bromide.

What is claimed is:

1. A process comprising heating a perfluoropolyether secondary halide, at a temperature at or above 220° C. to effect the production of a perfluoropolyether comprising at least one bromine or iodine in the primary position of one or more end groups of the perfluoropolyether.

2. A process according to claim 1 wherein said process is carried out under a condition or in a medium tat is substantially free of a solvent or iodine or both.

3. A process comprising contacting a perfluoropolyether acid fluoride with a metal bromide or metal iodide, wherein said metal bromide or metal iodide is selected from the group consisting of lithium, calcium, barium, aluminum, boron, and combinations of two or more thereof mixed metal bromides, mixed metal iodides, or combinations thereof at a temperature at or above 220° C. to effect the production of a perfluoropolyether, which comprises at least one bromine or iodine at the primary position of one or more end groups.

4. A process according to claim 3 wherein said perfluoropolyether acid fluoride comprises an acid fluoride moiety having the formula of COF at a secondary position of the perfluoropolyether acid fluoride.

5. A process according to claim 3 wherein said perfluoropolyether acid fluoride comprises a $CF_2OCF(CF_3)COF$ moiety.

6. A process according to claim 3 wherein said perfluoropolyether acid fluoride is a mionoacid fluoride or diacid fluoride.

7. A process according to claim 3 wherein said process comprises contacting said perfluoropolyether with mixed metal bromides, mixed iodides or combinations thereof.

8. A process according to claim 7 wherein said process is carried out substantially free of a solvent.

9. A process according to claim 3 wherein said perfluoropolyether comprises repeat units derived from $—CF(CF_3)CF_2O—$.

10. A process according to claim 3 wherein the perfluoropolyether of said perfluoropolyether acid fluoride comprises repeat units derived from the group consisting of $—CF_2O—$, $—CF_2CF_2O—$, $—CF_2CF(CF_3)O—$, $—CF(CF_3)O—$, $—CF(CF_3)CF_2O—$, $—CF_2CF_2CF_2O—$, $—CF(CF_5)O—$, $—CF_2CF(CF_5)O—$, $—CF_2CF(CF_2CF_3)O—$, $—CF_2CF(CF_2CF_2CF_3)O—$, $—CF(CF_2CF_3)O—$, $—Cf(CF_2CF_2CF_3)O—$, $—CH_2CF_2CF_2O—$, $—CF(Cl)CF_2CF_2O—$, $—CF(H)CF_2CF_2O—$, $CCl_2CF_2CF_2O—$, $—CH(Cl)CF_2CF_2O—$, and combinations of two or more thereof.

11. A process comprising contacting a perfluoropolyether primary iodide with carbon tetrabromide a temperature at or above about 180° C. to produce a primary perfluoropolyether primary bromide.

* * * * *

UNITED STATES PATENT AND TRADEMARK OFFICE
CERTIFICATE OF CORRECTION

PATENT NO.         : 7,148,385 B2
APPLICATION NO. : 10/626972
DATED                 : December 12, 2006
INVENTOR(S)        : Jon Lee Howell et al.

It is certified that error appears in the above-identified patent and that said Letters Patent is hereby corrected as shown below:

On The Title Page, Item (54), delete "LODIDES" and substitute therefor -- IODIDES --.

Col. 7, line 13, delete "tat" and substitute therefor -- that --.

Col. 7, line 16, delete "with a metal bromide or metal iodide" and insert this phrase in Col. 7, line 20, after the words "combinations thereof".

Col. 8, line 2, delete "mionoacid" and substitute therefor -- monacid --.

Col. 8, line 21, delete "–Cf(" and substitute therefor -- -CF( --.

Signed and Sealed this

Twentieth Day of November, 2007

JON W. DUDAS
*Director of the United States Patent and Trademark Office*